United States Patent [19]
Alferness et al.

[11] Patent Number: 5,387,233
[45] Date of Patent: Feb. 7, 1995

[54] INTRAVENOUS CARDIAC LEAD WITH IMPROVED FIXATION AND METHOD

[75] Inventors: Clifton A. Alferness; John R. Helland, both of Redmond, Wash.

[73] Assignee: InControl, Inc., Redmond, Wash.

[21] Appl. No.: 147,330

[22] Filed: Nov. 3, 1993

Related U.S. Application Data

[63] Continuation-in-part of Ser. No. 2,138, Jan. 11, 1993, abandoned.

[51] Int. Cl.⁶ .............................................. A61N 1/05
[52] U.S. Cl. .................................... 607/126; 607/122
[58] Field of Search ............... 607/126, 122, 119, 116, 607/115, 118; 128/642; 604/104–109

[56] References Cited

U.S. PATENT DOCUMENTS

| | | | |
|---|---|---|---|
| 4,154,247 | 5/1979 | O'Neill | 607/125 |
| 4,414,986 | 11/1983 | Dickhudt et al. | |
| 4,706,671 | 11/1987 | Weinrib | 604/104 |
| 4,825,871 | 5/1989 | Cansell | 607/2 |
| 4,852,573 | 8/1989 | Kennedy | 607/116 |
| 4,860,769 | 8/1989 | Fogarty et al. | 607/119 |
| 5,016,808 | 5/1991 | Heil, Jr. et al. | 607/122 |
| 5,170,802 | 12/1992 | Mehra | 607/126 |
| 5,221,261 | 6/1993 | Termin et al. | 604/104 |
| 5,235,977 | 8/1993 | Hirschberg et al. | 607/123 |
| 5,256,146 | 10/1993 | Ensminger et al. | 604/104 |
| 5,279,299 | 1/1994 | Imran | 607/126 |

*Primary Examiner*—William E. Kamm
*Assistant Examiner*—Kennedy J. Schaetzle
*Attorney, Agent, or Firm*—Richard O. Gray, Jr.

[57] ABSTRACT

An intravenous lead for use with a cardiac device implantable beneath the skin of a patient provides positive fixation for the lead when implanted in an artery or vein of the heart. The lead includes a lead body adapted to be fed into an artery or a vein of the heart of a patient and at least one electrode carried by the lead body and adapted to be coupled to the implantable cardiac device. The lead body includes a preformed section having a resiliently coiled configuration. The coiled section makes substantially continuous surface contact with inner wall surfaces of the artery or vein after the lead is implanted within the artery or vein for providing positive fixation of the lead.

18 Claims, 3 Drawing Sheets

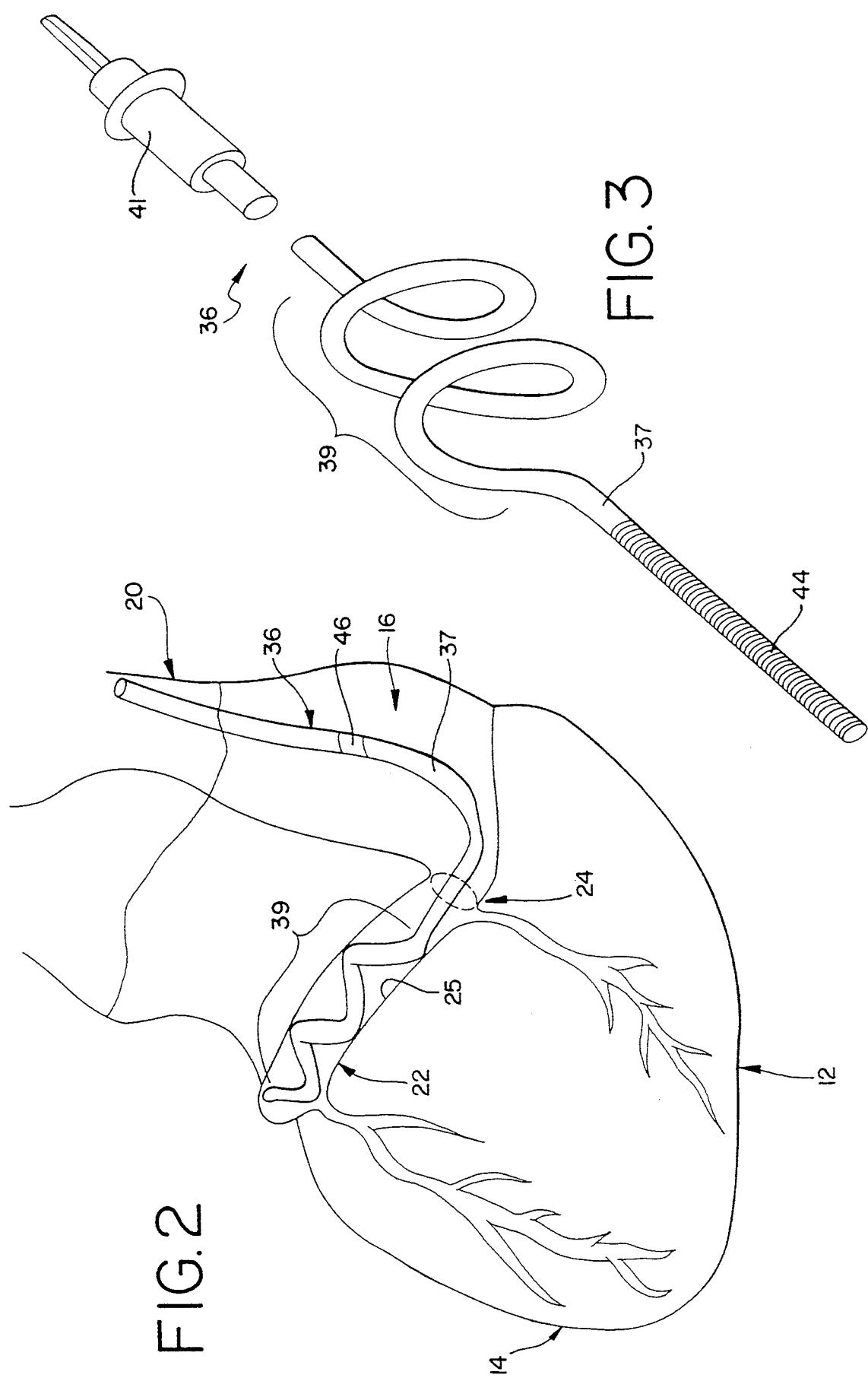

INTRAVENOUS CARDIAC LEAD WITH IMPROVED FIXATION AND METHOD

RELATED APPLICATION

This is a continuation-in-part of co-pending application Ser. No. 08/002,138, filed Jan. 11, 1993, abandoned.

BACKGROUND OF THE INVENTION

The present invention generally relates to an intravenous cardiac lead and method having an improved configuration for fixing the lead in a desired position within a vein or an artery after implantation. The present invention is more particularly directed to such an intravenous lead for use with an implantable atrial defibrillator which provides cardioverting electrical energy to the atria of the heart when the heart is in need of cardioversion. The intravenous cardiac lead of the present invention is particularly adapted for implantation in the coronary sinus of the heart and includes at least one electrode adapted to be within the coronary sinus or great vein of the heart and a second electrode adapted to be within the right atrium of the heart when the lead is fed into the heart to a preferred position to enable the sensing of atrial activity of the heart and the delivery of the cardioverting electrical energy to the atria.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved implantable atrial defibrillators and lead systems which exhibit automatic operation are fully described in copending U.S. applications, Ser. No. 07/685,130, filed Apr. 12, 1991, in the names of John M. Adams and Clifton A. Alferness for IMPROVED ATRIAL DEFIBRILLATOR AND METHOD, now U.S. Pat. No. 5,282,837, and Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention and incorporated herein by reference. The atrial defibrillators disclosed in the aforementioned referenced applications are truly automatic by including an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardioverter stage to deliver defibrillating or cardioverting electrical energy to the atria in timed relation to a detected ventricular electrical activation (R wave) of the heart. As a result, the atria are automatically and safely cardioverted.

As also disclosed in the aforementioned cross-referenced application, the quantity of electrical energy which is required to cardiovert or defibrillate the atria is reduced by an intravenous lead having an electrode adapted to be within the right atrium and another electrode adapted to be within the coronary sinus beneath the left atrium. The application of the cardioverting electrical energy across these electrodes not only reduces the energy required to cardiovert the atria, but also reduces the amount of energy applied to the ventricles. To place the electrodes in the positions noted above, the lead is fed down the superior vena cava, into the right atrium, through the coronary sinus ostium, and advanced into the coronary sinus.

While the lead is preshaped to conform to the above noted path after implantation to fix the lead in place, it would be desirable to provide the lead with more positive fixation since the blood flow through the coronary sinus is in a direction which tends to force the lead in a reverse direction with respect to the implantation feed path. Such positive fixation, however, must permit adequate blood flow through the coronary sinus and not cause occlusions.

The present invention provides such positive fixation for an intravenous lead such as the lead described above. In accordance with the present invention, the lead fixation is provided by a preformed section of the lead which has a resiliently coiled configuration. After the lead is implanted within a vein or an artery, the preformed section is permitted to assume its coiled configuration for making substantially continuous surface contact with inner wall surfaces of the artery or vein in the region of the coiled section. Such surface contact fixes the lead in place. Thereafter, fibrous tissue which builds up around the lead assures permanent fixation.

SUMMARY OF THE INVENTION

The present invention therefore provides an intravenous lead for use with a cardiac device implantable beneath the skin of a patient. The lead includes a lead body adapted to be fed into an artery or a vein of the heart of a patient and at least one electrode carried by the lead body and adapted to be coupled to the implantable cardiac device. The lead body includes a coiled section adapted to make substantially continuous surface contact with inner wall surfaces of the artery or vein.

The present invention further provides a method of implanting an intravenous cardiac lead within an artery or a vein of the human heart. The method includes the steps of providing a cardiac lead having a flexible lead body and feeding the lead body to a predetermined position within the artery or vein of the heart. The method further includes the step of imparting a coiled configuration to the lead body for making substantially continuous surface contact with inner wall surfaces of the artery or vein.

The present invention further provides a lead for use with a cardiac device implantable beneath the skin of a patient. The lead includes an inner styler coil, an outer electrically insulative jacket coaxial with and overlying the inner styler coil, and an elongated electrode overlying the electrically insulative jacket. One or both of the inner stylet coil and the elongated electrode includes a coiled portion for imparting a coiled configuration to the lead within a section of the lead corresponding to the coiled portion. As a result, after the lead is fed into an artery or vein of the patient, the coiled section of the lead makes substantially continuous surface contact with the inner wall surfaces of the artery or vein for retaining the lead within the artery or vein.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 2 is a posterior view of the heart with portions broken away to illustrate the fixation properties of an intravenous lead embodying the present invention;

FIG. 3 is a perspective exploded view of an intravenous lead embodying the present invention;

DETAILED DESCRIPTION OF THE PREFERRED EMBODIMENTS

Figure 1:
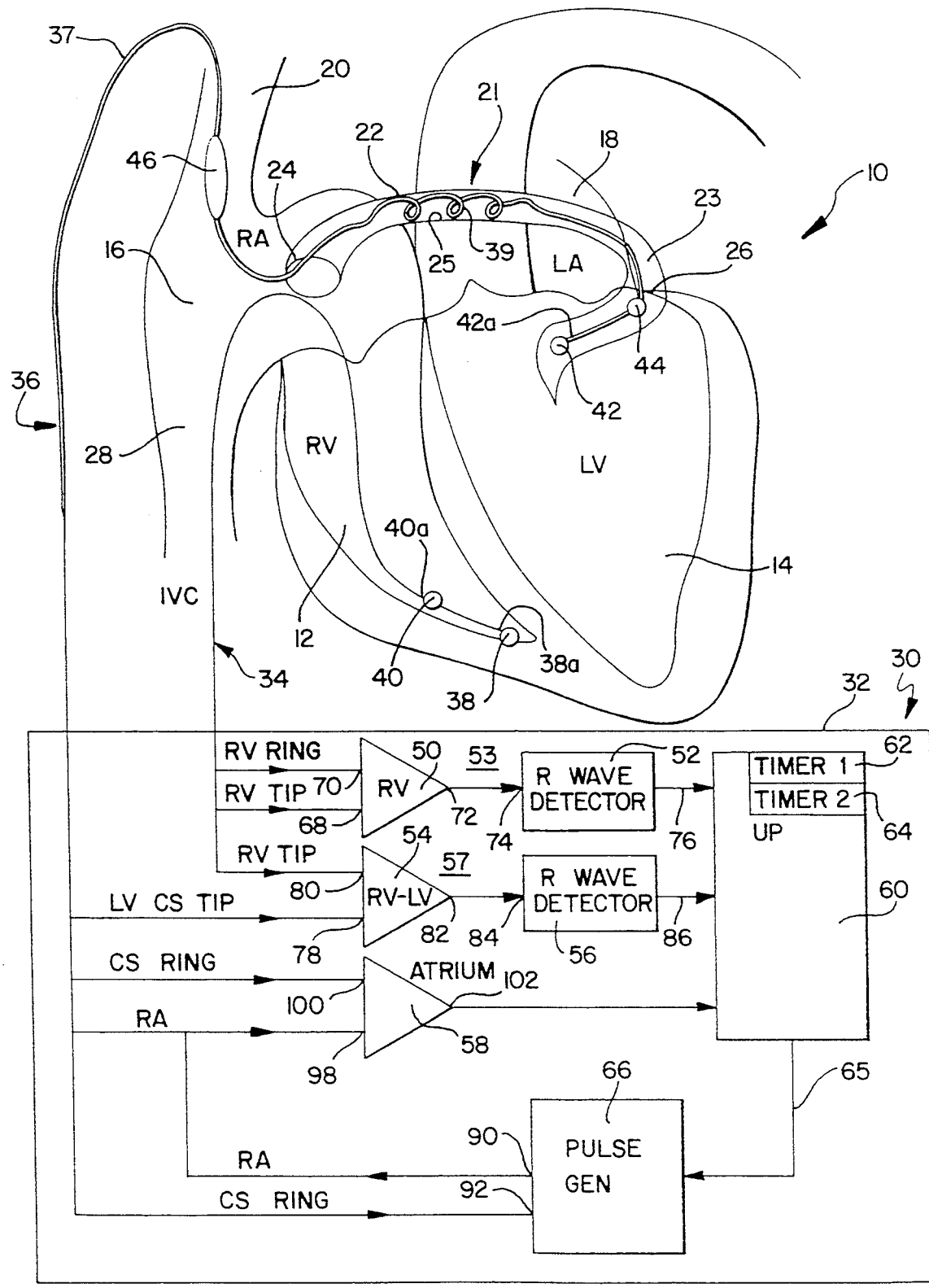
FIG. 1 is a schematic block diagram of a fully implantable atrial defibrillator shown in use with an intravenous lead embodying the present invention and in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26, and the inferior vena cava 28. In addition, as used herein, the term "ventricular electrical activations" denotes R waves of the heart cardiac cycle which induce depolarizations of the ventricles 12 and 14.

The atrial defibrillator 30 includes circuitry to be described herein after which is contained within an enclosure 32 for hermetically sealing the internal circuit elements of the atrial defibrillator. The atrial defibrillator is shown in use with an endocardial first lead 34, and an intravenous second lead 36 embodying the present invention. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular electrical activations (R waves) in the right ventricle between a first pair of locations 38a and 40a within the right ventricle 12. As illustrated, the lead 34 is fed through the inferior vena cava 28, into the right atrium 16, and then into the right ventricle 12. As will be appreciated by those skilled in the art, a second path for lead 34 could alternatively be through the superior vena cava 20, into the right atrium 16, and then into the right ventricle 12.

The second or intravenous lead 36 embodying the present invention generally includes a lead body 37 which carries a distal electrode 42, a ring electrode 44, and a proximal electrode 46. As illustrated, the lead body 37 is flexible and includes a preformed section 39 having a resiliently coiled configuration. Because the lead body 37 is flexible, the preformed section 39 may be elongated during implantation to reduce its effective cross-sectional diameter dimension to permit the lead 36 to be passed down the superior vena cava 20, into the right atrium 16, into the coronary sinus ostium 24, and advanced into the coronary channel 21 of the heart near the left side to a predetermined position where the electrode 44 is within either the coronary sinus 22 or the great cardiac vein 23 beneath the left atrium 18 near the left ventricle 14. The electrodes are preferably spaced apart relative to one another on lead body 37 so that when electrode 44 is positioned as described above, distal electrode 42 (which is distal to ring electrode 44) is within the coronary sinus 22 or great cardiac vein 23 adjacent the left ventricle 14 near the left ventricular wall 26 and electrode 46 is within the right atrium 16 after the preformed resilient coiled section 39 is permitted to assume its coiled configuration through the release of the elongation of section 39. As can be noted from the figure, the section 39 is proximal to electrode 44 and upon release of its elongation, assumes its coiled configuration within the coronary sinus 22. As a result, upon such release, the section 39 makes substantially continuous surface contact with the inner wall surfaces 25 of the coronary sinus 22. This surface contact serves to provide positive fixation of lead 36 in the position illustrated. In addition, the contact between lead body 37 and the inner wall surface of the coronary sinus 22 promotes the growth of fibrous tissue around the lead body in the region of section 39 for permanent fixation of the lead 36.

The distal electrode 42 of lead 36 and the electrode 38 of the first lead 34 permit bi-polar sensing of ventricular electrical activations (R waves) between a second pair of locations 38a and 42a of the heart. Alternatively, the second pair of electrodes for sensing R waves may include electrodes 44 and 38, in which case, electrode 42 may be eliminated. As will be noted in FIG. 1, the spacing between the second pair of locations 38a and 42a is greater than the spacing between the first pair of locations 38a and 40a. As fully disclosed in copending application Ser. No. 07/861,184, filed on Mar. 31, 1992, in the names of John M. Adams, Clifton A. Alferness and K. Ross Infinger for IMPROVED APPARATUS AND METHOD FOR RELIABLY DETECTING A DEPOLARIZATION ACTIVATION WAVE OF THE HEART AND ATRIAL DEFIBRILLATOR UTILIZING SAME, which application is assigned to the assignee of the present invention, these relative spacings between the first and second pairs of locations between which ventricular electrical activations are sensed enable reliable detection of R waves in accordance with the present invention.

The ring electrode 44 together with the proximal electrode 46 of lead 36 provide for the delivery of defibrillating or cardioverting electrical energy to the atria. Because the ring electrode 44 is located beneath the left atrium 18 near the left ventricle 14 and the proximal electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized.

Within the enclosure 32, the atrial defibrillator 30 includes a first sense amplifier 50, a first R wave detector 52, a second sense amplifier 54, a second R wave detector 56 and a third sense amplifier 58. Within the enclosure 32, the atrial defibrillator 30 also includes a microprocessor 60 and a pulse generator 66. As also can be seen in FIG. 1, the microprocessor 60 includes a first timer 62 and a second timer 64.

The first sense amplifier 50 includes a first input 68 which is coupled to electrode 38 of the first lead 34 and a second input 70 which is coupled to electrode 40 of the first lead 34. The first sense amplifier 50 thus senses the electrical activity of the heart 10 between the first pair of locations of the heart 38a and 40a. It amplifies the sensed electrical activity of the heart and provides at an output 72 an amplified signal or first electrocardiogram representative of the electrical activity of the heart sensed by the bi-polar electrodes 38 and 40.

The first R wave detector 52 includes an input 74 which is coupled to the output 72 of the first amplifier 50. The R wave detector 52 includes a threshold circuit which provides a substantially constant first electrical output having a duration substantially equal to the duration of the ventricular electrical activations (R waves) sensed between electrodes 38 and 40.

The second sense amplifier 54 includes a first input 78 which is coupled to the distal electrode 42 of lead 36 and a second input 80 which is coupled to electrode 38 of lead 34. As a result, the second sense amplifier 54 senses the electrical activity of the heart between the second pair of locations of the heart 38a and 42a. It provides at an output 82 an amplified signal or second electrocardiogram representative of the electrical activity of the heart sensed between the second pair of locations of the heart 38a and 42a.

The second R wave detector 56 includes an input 84 for receiving the amplified signal provided from the output 82 of the second sense amplifier 54. The second R wave detector 56 also includes a threshold circuit for providing a substantially constant second electrical output at output 86 having a duration substantially equal to the duration of the ventricular electrical activations sensed by the second sense amplifier 54.

When the heart 10 is in need of cardioversion or defibrillation, the first timer 62 times the duration of the first electrical output provided by the first R wave detector 52 for timing the duration of a ventricular electrical activation (R wave) sensed between the first pair of locations 38a and 40a. The second timer 64 also times the duration of the second electrical output provided by the second R wave detector 56 for timing the duration of the same ventricular electrical activation (R wave) sensed between the second pair of locations 42a and 38a. Since the spacing between the second pair of locations 42a and 38a is greater than the spacing between the first pair of locations 40a and 38a, if the electrical activity of the heart sensed by the first sensing means 53 and second sensing means 57 is a true ventricular electrical activation (R wave), the duration of the second electrical output provided by R wave detector 56 will be longer than the duration of the first electrical output provided by the first R wave detector 52.

If the second electrical output is longer in duration than the first electrical output, the microprocessor 60 immediately provides an indication signal on line 65 indicating that a ventricular electrical activation (R wave) has been detected. The pulse generator 66 is of the type well known in the art which includes a storage capacitor for storing an electrical charge. Upon receiving the indication signal from the microprocessor 60 over line 65, the pulse generator 66 delivers electrical cardioverting energy to the atria of the heart. To that end, the pulse generator 66 includes a first output 90 which is coupled to proximal electrode 46 of lead 36 and a second output 92 which is coupled to ring electrode 44 of lead 36. As a result, the electrodes 44 and 46 of the second lead 36 apply the electrical cardioverting energy provided by the pulse generator 66 to the atria 16 and 18 of the heart 10.

To determine when cardioversion or defibrillation of the atria of the heart 10 is required, the third sense amplifier 58 senses electrical activity in the atria 16 and 18 of the heart 10. To that end, the third sense amplifier 58 includes a first input 98 which is coupled to proximal electrode 46 and a second input 100 which is coupled to ring electrode 44. The third sense amplifier 58 includes an output 102 which is coupled to the microprocessor 60 for providing the microprocessor 60 with an amplified signal representing the electrical activity of the atria 16 and 18 of the heart.

The microprocessor 60, as described in the aforementioned copending U.S. applications Ser. Nos. 07/685,131 and 07/856,514, digitizes the amplified electrical signal provided by the third sense amplifier 58 and processes the digitized values of the atrial activity for detecting atrial fibrillation. Such atrial fibrillation detection may be implemented by the microprocessor 60 as described in the aforementioned copending applications.

Referring now to FIG. 2, it is a posterior view of the heart illustrating, from the posterior perspective, the feed path of lead 36. The portions of the heart illustrated in FIG. 2 are identified with the same reference numerals as used in connection with FIG. 1.

As will be appreciated by those skilled in the art, the lead 36 may be implanted as illustrated using the prior art technique of sliding a guide wire or stylet into a central passageway of the lead. The guide wire may be preshaped to assist in guiding the lead 36 along the path previously described. The stylet not only serves to guide or steer the lead 36 along the desired path, but in addition, serves to elongate coiled section 39 to reduce its effective cross-sectional diameter dimension to permit the lead to be fed into the heart. Once the lead reaches a predetermined position within the heart, such as, for example, corresponding to the ring electrode 44 (FIG. 1) being located either within the coronary sinus 22 or the great cardiac vein 23 near the left ventricular free wall 26, the guide wire is retracted from the lead.

The retraction of the guide wire from the lead 36 releases the elongation of the coiled section 39 permitting the coil section to resiliently assume its coiled configuration as illustrated. Upon assuming its coiled configuration, the coiled section 39 will have a cross-sectional outer diameter dimension corresponding to the inner diameter dimension of the artery or vein in which it resides and in accordance with this preferred embodiment, the inner diameter dimension of the coronary sinus 22.

As a result of the foregoing, the coiled section 39 will make substantially continuous surface contact with the inner surface 25 of the coronary sinus 22. This contact, together with the force exerted by the coiled section 39 against the inner wall surface 25 of the coronary sinus 22, provides positive fixation of lead 36. Also, as a result of the surface contact between coiled section 39 and the inner surface 25 of the coronary sinus 22, fibrous tissue will grow around the lead body 37 in the region of the coiled section 39 to provide permanent fixation of lead 36.

Even though the coiled section 39 provides positive fixation of lead 36, it will not adversely effect blood flow through the coronary sinus 22. Blood within the coronary sinus 22 will freely flow through the inner diameter dimension of the coiled section 39. Also, because of such free flow, the formation of occlusions through blood clotting will not occur.

Referring now to FIG. 3, it shows the lead 36 embodying the present invention in an exploded partial perspective view.

In addition to the structural elements of lead 36 previously described, the lead 36 further includes a connector 41 at its proximal end for coupling the electrodes, such as ring electrode 44, carried by lead body 37 of lead 36 to an implantable cardiac device such as atrial defibrillator 30 of FIG. 1.

The lead body 37 may be formed from flexible material such as polyurethane or silicone rubber. When the lead body 37 is formed from polyurethane, the coiled section 39 may be preformed by heat treating and thermal setting in a manner known in that art. Alternatively, if the lead body 37 is formed from silicone rubber, the coiled section 39 may be preformed by injection molding only coiled section 39 to its desired shape as also known in that art.

The configuration of coiled section 39 as illustrated is preferably a spiral configuration but other configurations are also contemplated by the present invention, such as for example, a serpentine configuration. Preferably, the coiled section is formed to have a free form cross-sectional outer diameter of, for example, eight (8) to twelve (12) millimeters. Also, although the coiled section 39 illustrated in FIG. 3 includes two loops, the coiled section 39 may have any number of loops as appropriate for a given application.

Figure 4:
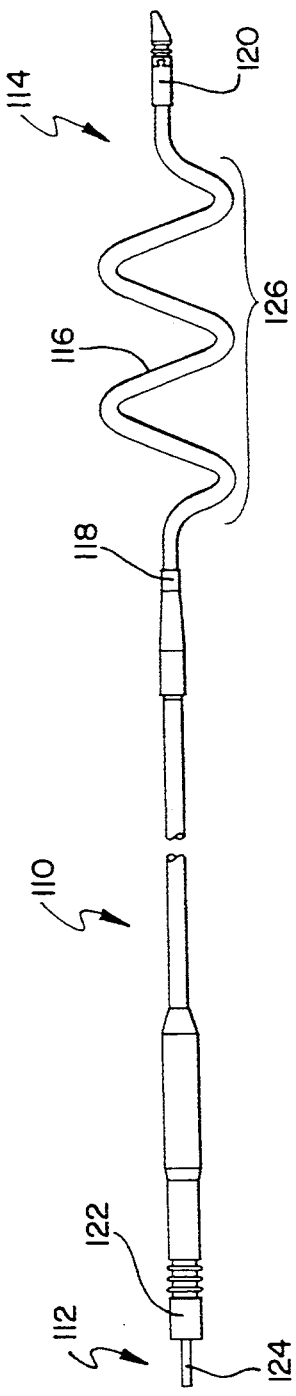
FIG. 4 is a side plan view of another lead embodying the present invention.

Referring now to FIG. 4, it illustrates, in side plan view, another lead 110 embodying the present invention. The lead 110 includes a proximal end 112 and a distal end 114. At the distal end 114 is an elongated electrode 116 which extends between a proximal electrode header 118 and a distal electrode header 120. At the proximal end 112, the lead 110 includes a connector 122 having a pin 124 which is coupled to the electrode 116 and which provides electrical connection to an implanted cardiac device, such as an atrial defibrillator.

The lead 110 is particularly adapted for use with an atrial defibrillator and for disposing the electrode 116 in the coronary sinus and great cardiac vein of the heart. As will be noted in FIG. 4, the lead 110 has a coiled configuration in a section 126 of the lead 110 which includes the elongated electrode 116. The coiled configuration of the lead 110 in the section 126 may be obtained in a manner as more clearly illustrated in FIG. 5.

Figure 5:
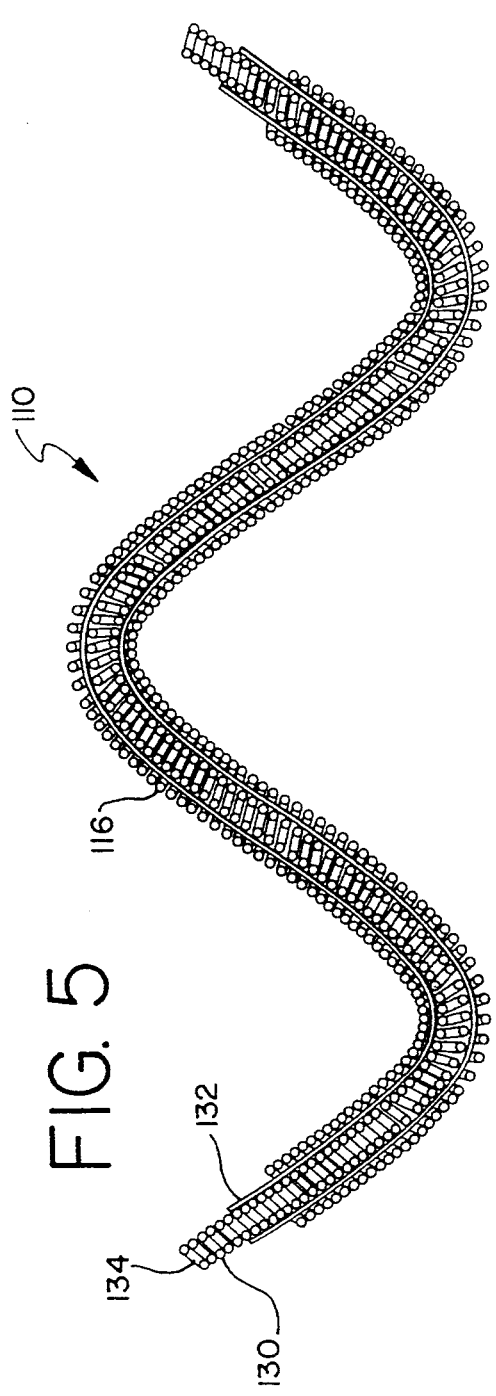
FIG. 5 is a partial, cross-sectional view, of the lead of FIG. 4.

FIG. 5 is a partial cross-sectional view of the lead 110 within the section 126. More specifically, FIG. 5 shows in cross section one coil turn of the coiled configuration of the lead 110 within the coiled section 126. The lead 110, as illustrated in FIG. 5, includes an inner stylet coil 130, an outer electrically insulative jacket 132, and the elongated electrode 116.

The stylet coil 130 is formed by a plurality of closely spaced small diameter turns of wire. The stylet coil 130 thus includes a central passageway 134 into which a stylet may be extended prior to and during the implantation of the lead 110.

The outer jacket 132 is formed of an electrically insulative material such as polyurethane or silicone rubber. As will be noted in the figure, the insulative jacket 132 is coaxial with and overlies the inner stylet coil 130.

The electrode 116, like the stylet coil 130, is also formed from a plurality of closely spaced turns of a conductive wire. The electrode 116 is preferably preformed with its closely spaced turns prior to being mounted upon the lead 110.

To impart the coiled configuration to the lead 110 within the section 126 as illustrated in FIG. 4, either one or both of the elongated electrode 116 and the inner stylet coil 130 is coiled in a portion thereof corresponding to the section 126 having the coiled configuration. To that end, the stylet coil 130 may be coiled to form a helix having comparatively widely spaced turns before the insulative jacket 132 is slid over the stylet coil 130. Similarly, the electrode 116 may be coiled to form a helix having comparatively widely spaced turns prior to the electrode 116 being slid over the insulative jacket 132. With either construction, the lead 110 within the section 126 will be imparted with a coiled configuration for making substantially continuous surface contact with inner wall surfaces of the artery or vein for retaining the lead within the artery or vein in which it is implanted.

Figure 6:
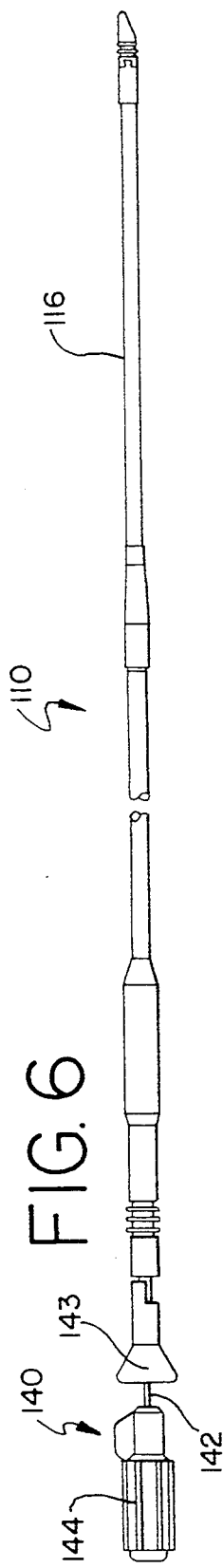
FIG. 6 is another side plan view of the lead of FIG. 4 with a stylet inserted therein prior to implantation.

Referring now to FIG. 6, FIG. 6 illustrates the lead 110 having a stylet 140 inserted therein prior to the implantation of the lead 110. The stylet includes a stylet wire 142 and a stylet handle 144. As will be noted in FIG. 6, when the stylet wire 142 is inserted through a funnel-shaped stylet guide 143 into the central passageway of the lead 110 formed by the stylet coil 130, the coiled section 126 is elongated so as to render the lead 110 feedable into the artery or vein of the heart. Once the lead is in its desired position, the stylet 142 is removed for releasing the elongation of the preformed coiled section 126 of the lead. As a result, the preformed coiled section 126, which, in accordance with this preferred embodiment, includes electrode 116, will make substantially continuous surface contact with inner wall surfaces of the artery or vein for retaining the lead 110 within the artery or vein.

Hence, once the elongation of the preformed coiled section 126 is released, the section 126 is permitted to assume the coiled configuration. Further, the coiled configuration may be imparted to the lead 110 by either the stylet coil 130 being preformed in a coiled configuration or the electrode 116 being preformed in a coiled configuration as previously described.

While particular embodiments of the present invention have been shown and described, modifications may be made. For example, while the coiled section 39 is preferably formed from a preformed section of the lead body 37, the coiled configuration of the lead body may be achieved by methods other than disclosed herein in accordance with the preferred embodiment. For example, a non-preformed flexible lead body may first be fed to a desired position within an artery or vein and thereafter, a further stylet having a coiled configuration may be introduced into the lead body to impart the desired coiled configuration to the lead body. Thereafter, the coiled stylet may be left in place within the lead body after implantation of the lead. It is therefore intended to cover in the appended claims all such changes and modifications which fall within the true spirit and scope of the invention.

What is claimed is:

1. An intravenous lead for use with a cardiac device implantable beneath the skin of a patient, said lead comprising:

an inner stylet coil;

an outer electrically insulative jacket coaxial with and overlying said inner stylet coil; and an electrode overlying said electrically insulative jacket, said inner stylet coil being coiled for forcing at least a section of said lead into a coiled configuration.

2. A lead as defined in claim 1 wherein said electrode is an elongated electrode.

3. A lead as defined in claim 2 wherein said lead has a distal end, and wherein said elongated electrode is located at said distal end of said lead.

4. A lead as defined in claim 2 wherein said elongated electrode overlies said coiled section.

5. A lead as defined in claim 4 wherein said lead has a distal end and wherein said coiled section and said elongated electrode are at said distal end of said lead.

6. A method of implanting an intravenous cardiac lead within an artery or a vein of the human heart, said method comprising the steps of:

providing a cardiac lead having a flexible lead body;

feeding said lead body to a predetermined position within the artery or vein of the heart; and imparting a coiled configuration to said lead body for making substantially continuous surface contact with inner wall surfaces of the artery or vein.

7. A method as defined in claim 6 wherein said providing step includes preforming a section of said lead body into a resiliently coiled configuration to form a preformed coiled section, wherein said feeding step includes feeding said lead body with said preformed coiled section elongated so as to be feedable into the artery or vein of the heart, and wherein said imparting step includes releasing the elongation of said preformed coiled section after the lead is fed to said predetermined position within the artery or vein of the heart to permit said preformed coiled section to assume said coiled configuration.

8. A method as defined in claim 7 wherein said providing step includes providing at least one electrode on said lead body with said preformed coiled section being proximal to said at least one electrode.

9. A method as defined in claim 8 wherein said providing step includes providing a second electrode on said lead body proximal to said preformed coiled section.

10. A method as defined in claim 9 wherein said predetermined position within the artery or vein of the heart corresponds to said at least one electrode being within the coronary sinus or great vein of the heart and wherein said providing step includes spacing apart said at least one electrode, said preformed coiled section, and said second electrode relative to one another such that when said at least one electrode is within the coronary sinus or great vein of the heart, said preformed coiled section is adapted to be within the coronary sinus of the heart and said second electrode is adapted to be within the right atrium of the heart.

11. A method as defined in claim 10 wherein said providing step further includes providing a distal electrode on said lead body with said at least one electrode being proximal to said distal electrode and spaced from said distal electrode such that when said at least one electrode is within the coronary sinus or great vein of the heart said distal electrode is adapted to be within the great vein of the heart.

12. A method as defined in claim 6 wherein said lead body includes an inner stylet coil, wherein said providing step includes preforming a section of said stylet coil into a coiled configuration to impart to said lead body a preformed resilient coiled section, wherein said feeding step includes feeding said lead body with said preformed resilient coiled section elongated so as to be feedable into the artery or vein of the heart, and wherein said imparting step includes releasing the elongation of said preformed resilient coiled section after the lead is fed to said predetermined position within the artery or vein of the heart to permit said preformed resilient coiled section to assume said coiled configuration.

13. A method as defined in claim 12 wherein said providing step includes providing an elongated electrode on said lead body overlying said preformed coiled section.

14. A method as defined in claim 13 wherein said lead has a distal end and wherein said providing step includes providing said elongated electrode on said lead body distal end.

15. A method as defined in claim 14 wherein said predetermined position within the artery or vein of the heart corresponds to said elongated electrode being within the coronary sinus or great vein of the heart.

16. A method as defined in claim 6 wherein said providing step includes providing an elongated electrode on said lead body and preforming a section of said elongated electrode into a coiled configuration to impart to said lead body a preformed resilient coiled section, wherein said feeding step includes feeding said lead body with said preformed resilient coiled section elongated so as to be feedable into the artery or vein of the heart, and wherein said imparting step includes releasing the elongation of said preformed resilient coiled section after the lead is fed to said predetermined position within the artery or vein of the heart to permit said preformed resilient coiled section to assume said coiled configuration.

17. A method as defined in claim 16 wherein said lead has a distal end and wherein said providing step includes providing said elongated electrode on said lead body distal end.

18. A method as defined in claim 17 wherein said predetermined position within the artery or vein of the heart corresponds to said elongated electrode being within the coronary sinus or great vein of the heart.

* * * * *